(12) United States Patent
Weber et al.

(10) Patent No.: US 10,369,385 B2
(45) Date of Patent: Aug. 6, 2019

(54) QUANTITATIVE MRI MEASUREMENTS NEAR METAL OBJECTS

(71) Applicant: The Board of Trustees of the Leland Stanford Junior University, Palo Alto, CA (US)

(72) Inventors: Hans Weber, Menlo Park, CA (US); Daehyun Yoon, Palo Alto, CA (US); Valentina Taviani, Palo Alto, CA (US); Brian A. Hargreaves, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 712 days.

(21) Appl. No.: 14/686,455

(22) Filed: Apr. 14, 2015

(65) Prior Publication Data
US 2016/0306021 A1 Oct. 20, 2016

(51) Int. Cl.
| | | |
|---|---|---|
| *G01V 3/00* | (2006.01) | |
| *A61N 7/02* | (2006.01) | |
| *A61N 1/40* | (2006.01) | |
| *A61B 5/055* | (2006.01) | |
| *G01R 33/48* | (2006.01) | |
| *G01R 33/50* | (2006.01) | |
| *G01R 33/565* | (2006.01) | |
| *A61B 18/12* | (2006.01) | |
| *A61B 5/06* | (2006.01) | |

(52) U.S. Cl.
CPC .............. *A61N 7/02* (2013.01); *A61B 5/055* (2013.01); *A61B 18/12* (2013.01); *A61N 1/403* (2013.01); *G01R 33/4804* (2013.01); *G01R 33/50* (2013.01); *G01R 33/56527* (2013.01); *A61B 5/062* (2013.01)

(58) Field of Classification Search
CPC ............ G01R 33/4816; G01R 33/4818; G01R 33/482; G01R 33/4822; G01R 33/4824; G01R 33/4826; G01R 33/4828; G01R 33/483; G01R 33/4831; G01R 33/4833; G01R 33/5608; G01R 33/561; G01R 33/5611; G01R 33/5612; G01R 33/5613; G01R 33/5614; G01R 33/5615; G01R 33/5616; G01R 33/56545; G01R 33/56554; G01R 33/56563; G01R 33/56572; G01R 33/56581; G01R 33/5659; G01R 33/567; G01R 33/5673; G01R 33/5676
USPC .................................................. 324/300–322
See application file for complete search history.

(56) References Cited

U.S. PATENT DOCUMENTS

| | | |
|---|---|---|
| 4,843,322 A | 6/1989 | Glover |
| 7,928,729 B2 | 4/2011 | Hargreaves et al. |

(Continued)

*Primary Examiner* — Giovanni Astacio-Oquendo
*Assistant Examiner* — Raul J Rios Russo
(74) *Attorney, Agent, or Firm* — Beyer Law Group LLP

(57) ABSTRACT

A method for providing at least one measurement by a magnetic resonance imaging (MRI) system of a tissue property or underlying tissue property in a region sufficiently close to a metal object, so that the metal object induces artifacts is provided. At least one magnetic resonance imaging signal from the region is acquired through the MRI system. The acquired at least one MRI signal is processed to correct for artifacts induced by the metal object. At least one tissue property or underlying tissue property measurement is extracted from the processed at least one MRI signal.

18 Claims, 7 Drawing Sheets

(56) References Cited

U.S. PATENT DOCUMENTS

| | | |
|---|---|---|
| 8,274,286 B2 | 9/2012 | Koch et al. |
| 2013/0119984 A1* | 5/2013 | Levy .................. G01R 33/4804 |
| | | 324/309 |
| 2013/0158387 A1* | 6/2013 | Tanttu ................ G01R 33/4804 |
| | | 600/411 |
| 2013/0301892 A1* | 11/2013 | Liu ...................... A61B 5/0033 |
| | | 382/131 |
| 2014/0002080 A1 | 1/2014 | Den Harder et al. |
| 2014/0005523 A1* | 1/2014 | Kohler .................. A61B 5/055 |
| | | 600/411 |
| 2014/0062474 A1* | 3/2014 | Zhou ...................... A61B 5/055 |
| | | 324/309 |
| 2015/0035531 A1* | 2/2015 | Stemmer ............ G01R 33/4836 |
| | | 324/309 |
| 2015/0073261 A1* | 3/2015 | Kohler ...................... A61N 7/02 |
| | | 600/411 |
| 2015/0190659 A1* | 7/2015 | Kohler ...................... A61N 7/02 |
| | | 600/411 |
| 2015/0272453 A1* | 10/2015 | Heberlein ............ A61B 5/0263 |
| | | 600/419 |
| 2016/0084931 A1* | 3/2016 | Bachschmidt ... G01R 33/56518 |
| | | 324/309 |
| 2016/0263404 A1* | 9/2016 | Mougenot ............ A61N 5/1067 |
| 2017/0371010 A1* | 12/2017 | Shanbhag ............ G01R 33/243 |

* cited by examiner

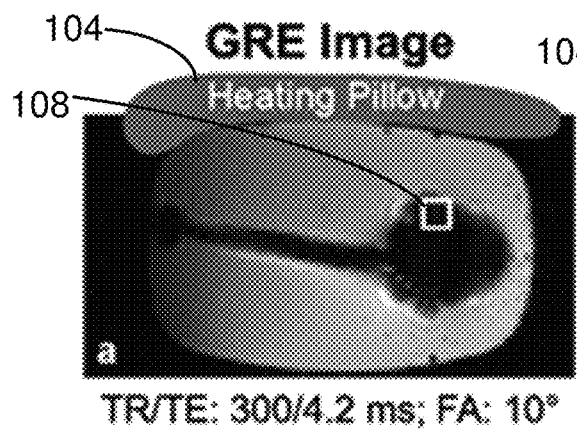
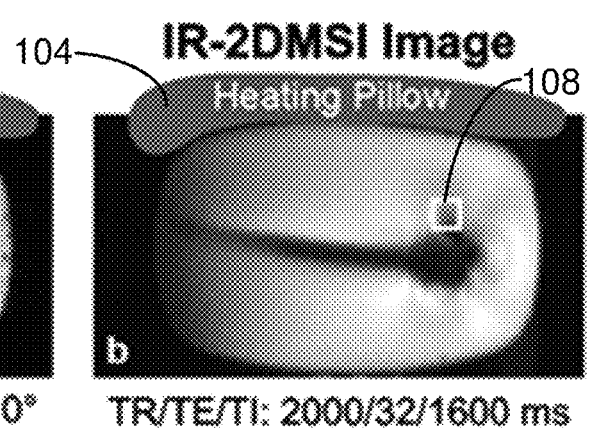
FIG. 1A  FIG. 1B
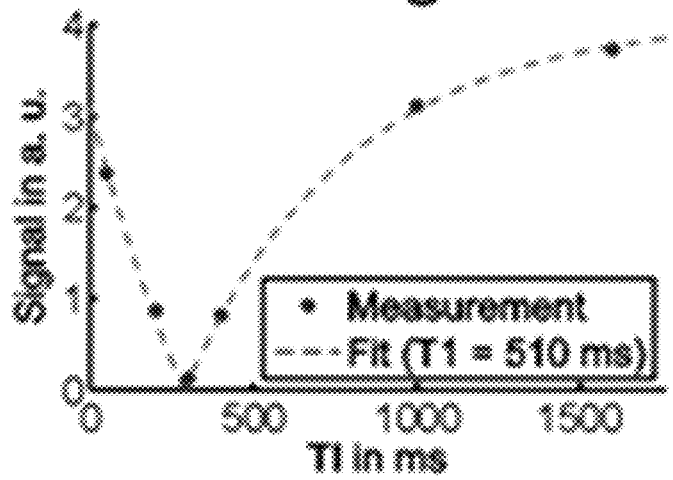
FIG. 2

QUANTITATIVE MRI MEASUREMENTS NEAR METAL OBJECTS

GOVERNMENT RIGHTS

This invention was made with Government support under contract EB017739 awarded by the National Institutes of Health. The Government has certain rights in the invention.

BACKGROUND OF THE INVENTION

This invention relates generally to magnetic resonance imaging (MRI). Magnetic resonance imaging (MRI) is a non-destructive method for the analysis of materials and is an approach to medical imaging. It is generally non-invasive and does not involve ionizing radiation. In very general terms, nuclear magnetic moments are excited at specific spin precession frequencies that are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

Magnetic resonance (MR) imaging is based on nuclear spins, which can be viewed as vectors in a three-dimensional space. During an MRI experiment, each nuclear spin responds to four different effects: precession about the main magnetic field, nutation about an axis perpendicular to the main field, and both transverse and longitudinal relaxation. In steady-state MRI experiments, a combination of these effects occurs periodically.

U.S. Pat. No. 4,843,322 to Glover, issued Jun. 27, 1989, which is incorporated by reference for all purposes, discloses a method for producing multi-slice MRI images. U.S. Pat. No. 7,928,729 to Hargreaves et al., issued Apr. 19, 2011, which is incorporated by reference for all purposes, discloses a distortion-free magnetic resonance imaging near metallic implants.

SUMMARY OF THE INVENTION

In accordance with the invention, a method for providing at least one measurement by an MRI system of a tissue property or underlying tissue property in a region sufficiently close to a metal object, so that the metal object induces artifacts is provided. At least one magnetic resonance imaging signal from the region is acquired through the magnetic resonance imaging (MRI) system. The acquired at least one MRI signal is processed to correct for artifacts induced by the metal object. At least one tissue property or underlying tissue property measurement is extracted from the processed at least one MRI signal.

The invention and objects and features thereof will be more readily apparent from the following detailed description and appended claims when taken with the drawings.

BRIEF DESCRIPTION OF THE DRAWINGS

FIG. 1A shows a GRE image and FIG. 1B shows an IR-2DMSI image of a phantom containing the metal shoulder replacement.

FIG. 2 depicts the measured IR-2DMSI signal variation over Time to Inversion (TI) for a voxel located within the ROI and the resulting fit.

DETAILED DESCRIPTION OF ILLUSTRATED EMBODIMENTS

Figure 3:
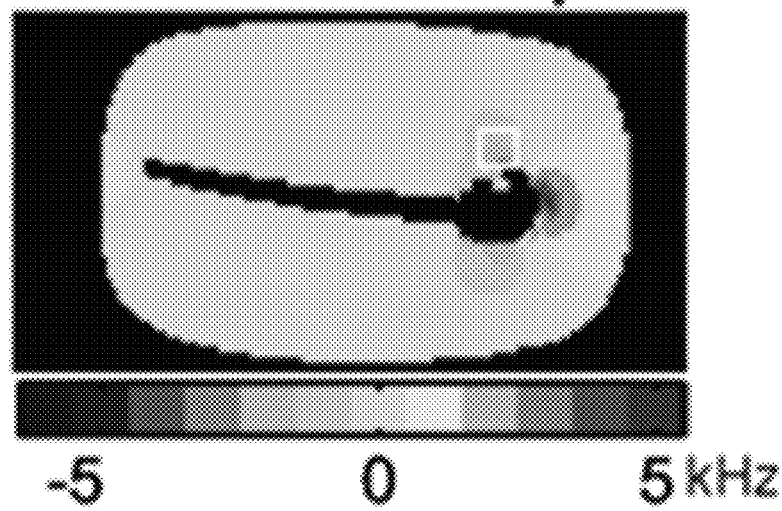
FIG. 3 is a local bin map showing the contribution of the individual bin T1 maps to the final T1 map.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Currently there is no technique available for MR thermometry near metal implants or surgical clips. Commonly used gradient-recalled echo (GRE) based techniques such as mapping of the proton resonance frequency (PRF) shift fail due to the strong signal dephasing and loss introduced by the associated field inhomogeneities, as shown in FIG. 1A. An embodiment of the invention provides MR thermometry near metal based on a multispectral imaging (MSI) approach and by exploiting the temperature dependence of the T1 relaxation time. Initial feasibility is demonstrated in phantom experiments.

Pulse Sequence:

In an embodiment for inversion recovery (IR) T1 mapping, a single-shot two dimensional MSI (2DMSI) technique was extended with a dedicated spatially selective inversion pulse matched to the excitation. 2DMSI enables fast artifact-reduced imaging near metal by reversing the selection gradient between excitation and refocusing pulses, resulting in the excitation of finite spectral and spatial regions, called bins, which can be imaged with minimal artifact and combined to build up the full image. A more detailed description of the 2DMSI technique is given below.

Data Acquisition: In this embodiment, all data acquisition was performed on a 3T whole body MRI system equipped with an 8 channel receiver coil and with a phantom containing a total shoulder replacement with a titanium shaft embedded in doped agar gel. For each T1 map, a series of six IR-2DMSI images with varying IR time was acquired (TR/TE/TI: 2000/32/50-1600 ms; field of view (FOV):

240×280 mm; slice thickness: 3 mm; matrix: 128×54 (half-Fourier and no parallel imaging); 12 bins, covering an excitation bandwidth of +/−5.4 kHz; duration per T1 map: ~4 min). A temperature gradient through the phantom was achieved by positioning a pillow heated by hot water on one side of the phantom. During a heating period of about 180 min, data for a total of 29 T1 maps was acquired. A fluoroptic temperature sensor with a precision of 0.1° C. located both within the imaged slice and close to the metal implant monitored the temperature increase in the phantom.

Data Analysis:

For each T1 map, fitting of the magnitude data was performed on a bin-by-bin basis using a four-parameter model also considering flip-angle imperfections. To improve SNR for fitting, the data was smoothed with a 3×3 kernel in image space. The final T1 map was composed from the individual bin T1 maps with the local T1 value provided by the bin with maximum local image intensity.

FIG. 1A shows a GRE image and FIG. 1B shows an IR-2DMSI image of a phantom containing the metal shoulder replacement. The position of the heating pillow 104 is shown above the phantom. The box 108 indicates the region of interest (ROI) placed around the temperature sensor. FIG. 1B demonstrates the capability of the 2DMSI technique for artifact-reduced imaging close to metal.

Figure 4:
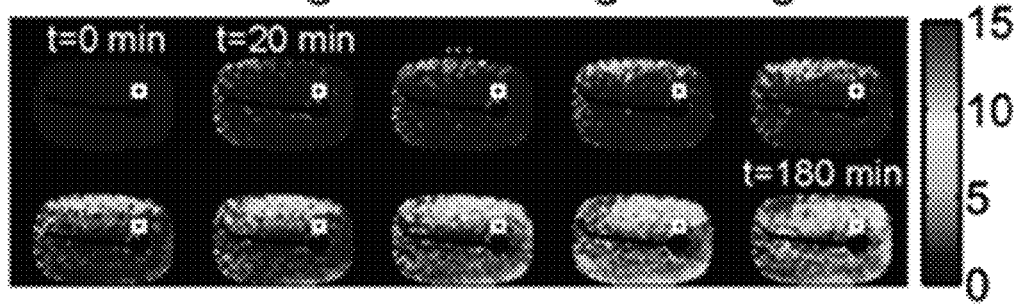
FIG. 4 shows the measured change in T1 during heating of the phantom for selected time steps corresponding to an interval of about 20 min.
Figure 5:
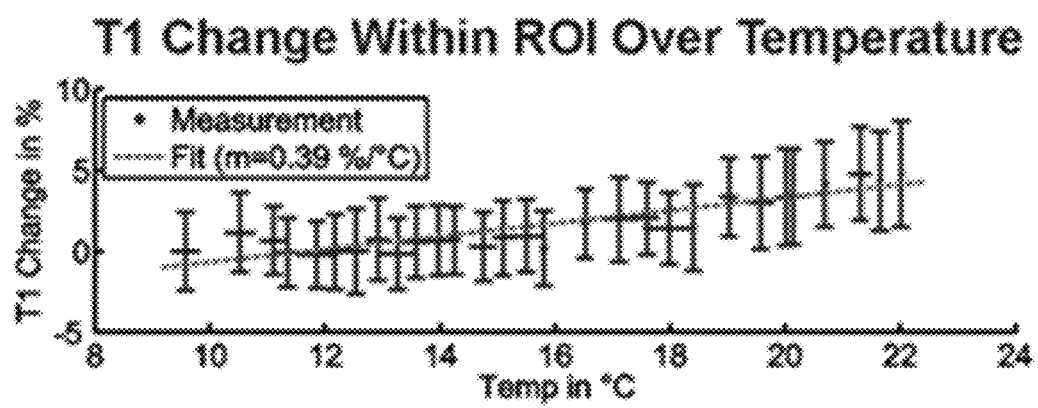
FIG. 5 presents the resulting change of the average T1 within the ROI for all 29 experiments over the temperature provided by the temperature sensor.

FIG. 2 depicts the measured IR-2DMSI signal variation over TI for a voxel located within the ROI and the resulting fit. FIG. 3 is a local bin map showing the contribution of the individual bin T1 maps to the final T1 map. FIG. 3 demonstrates the composition of the final T1 map from the individual bin T1 maps. FIG. 4 shows the measured change in T1 during heating of the phantom for selected time steps corresponding to an interval of about 20 min. T1 increases with ongoing heating and the increase is strongest close to the heating pillow. The T1 increase starts from the side facing the heating pillow and eventually spreads over the entire phantom. FIG. 5 presents the resulting change of the average T1 within the ROI for all 29 experiments over the temperature provided by the temperature sensor. The T1 variation (standard deviation) within the ROI corresponds to about 2% of the baseline ROI T1 value. The uncertainty range of the temperature measurement of up to 0.8° C. results from the ongoing heating during data acquisition. The fit assumes a linear increase of T1 over temperature. The results would support a temperature dependence of about 0.4%/° C. Within the GRE image of FIG. 1A, there is negligible signal at the position of the ROI.

The embodiment provides MR thermometry close to metal and thus in regions where conventional methods such as PRF shift mapping fail. The underlying 2DMSI technique provides the basis for artifact-reduced imaging while maintaining acceptable acquisitions times. Although the current temporal resolution of about 4 min is still long, it might be further reduced by optimizing the number of bins and/or the number of TI acquisitions. The full IR measurement applied in this work is beneficial as it also takes into account the temperature dependency of the equilibrium signal. However, "reusing" the long TI acquisition or using a proton-density-weighted signal are possibilities to accelerate acquisition.

Figure 6:
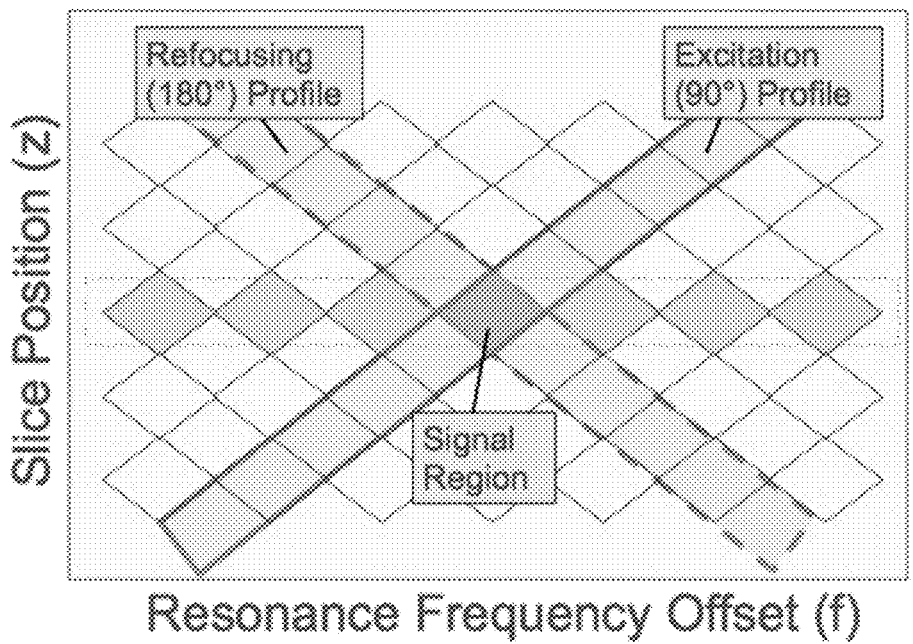
FIG. 6 shows reversing the selection gradient between excitation and refocusing pulses excites finite spectral (f) and spatial (z) regions ("bins").

In the following, the 2DMSI technique for fast 2D MR imaging with distortion correction near metal is described in more detail. Reversing the selection gradient between excitation and refocusing pulses excites finite spectral (f) and spatial (z) regions ("bins"), where frequency modulation of each pulse allows arbitrary positioning of regions, as shown in FIG. 6. Using a high readout bandwidth (BW) limits distortion to within about a pixel (slice BW/pixel BW ratio). Multiple bins at a location can be combined with a complex sum or square-root-sum-of-squares approach as with other MSI methods.

The steps are then simply as follows:
1) Excite and refocus a region with limited spectral and spatial extent.
2) Form a 2D image with a standard imaging sequence, demodulating the received signal at the center frequency of the excited and refocused region.
3) Combine the received images at a given spatial location by using a complex sum, magnitude sum, square-root sum-of-squares, or other combination process.

Aspects of this embodiment were demonstrated in a phantom with a titanium shaft/cobalt-chromium head shoulder replacement. In this embodiment, imaging was done at 3T with TR/TE=3000/12 ms, 2 mm-thick slices, 384×120 matrix over 24×18 cm FOV with ±125 kHz receive bandwidth, 1.3 kHz RF bandwidth, ETL=8, half-Fourier and no parallel imaging. The following cases of interest are demonstrated:

a) Single-slice imaging with 24 frequency bins in 32 sec compared to a 24-slice fast spin echo (FSE) scan.

b) Distortion-free imaging by exciting 24 frequency bins for each one of 24 slices (12:48) compared to a SEMAC scan with 24 slices and 24 z phase encodes in 9:22 (25% speedup using elliptical k-space sampling).

c) Using one y-projection image (Fourier transformed ky=0 line) for each bin to determine the signal in that bin to rapidly map where signal occurs. Automated selection of bins to include is done retrospectively using a threshold of 1% of the maximum bin signal. This selection could be prospective under the assumption that the excitation regions can be efficiently interleaved, resulting in a substantial scan time decrease.

Figure 7:
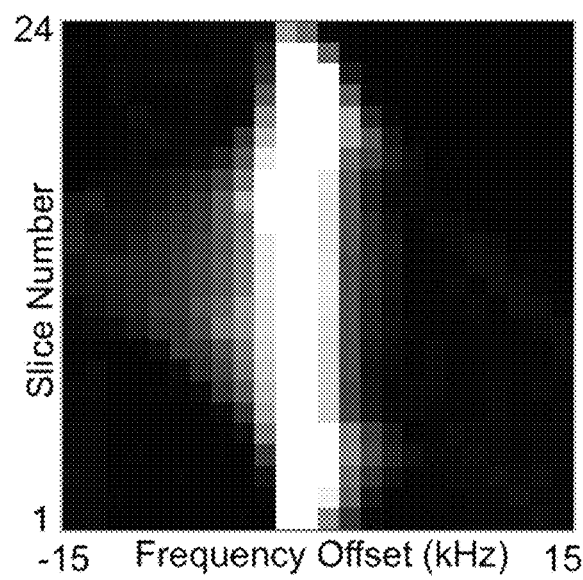
FIG. 7 shows the maximum intensity along the y-projection for each excited bin, which is used to automatically select bins and reduce scan time.
Figure 8:
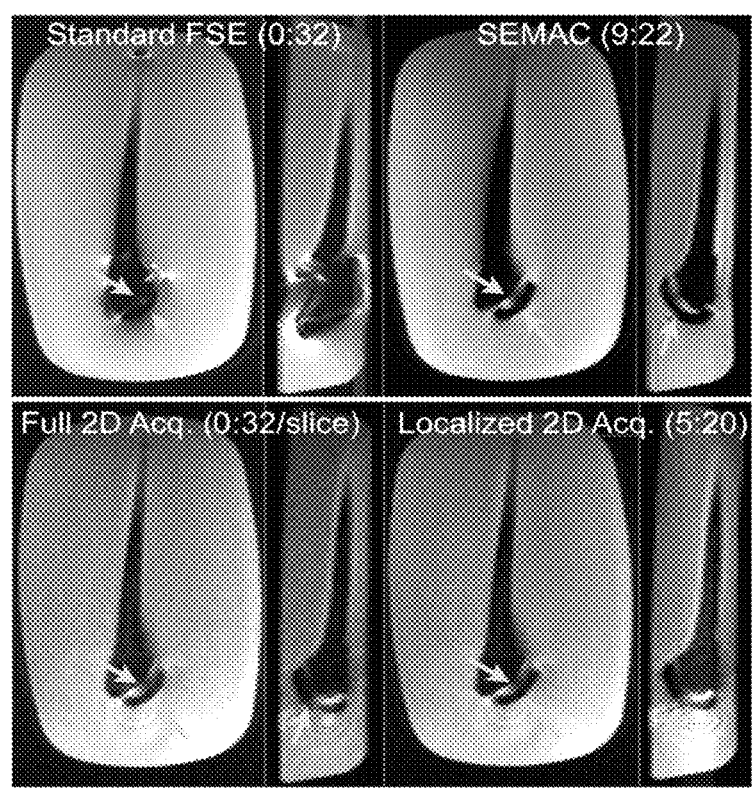
FIG. 8 compares standard FSE, SEMAC, a full acquisition with the proposed approach, and the reduced acquisition concept with retrospective discarding of bins below the 1% threshold.

FIG. 7 shows the maximum intensity along the y-projection for each excited bin, which is used to automatically select bins and reduce time. FIG. 8 compares standard FSE, SEMAC, a full acquisition with the proposed approach, and the reduced acquisition concept with retrospective discarding of bins below the 1% threshold. FIG. 8 shows coronal and sagital images from standard FSE, SEMAC, a full 2D acquisition of all bins, and bins with at least 1% of the maximum bin signal based on the localizer, shown in FIG. 7. Arrows show comparable recovery of the signal in the neck and at the rounded head with the latter 3 methods, despite an SNR trade-off. This is a proof-of-concept of the 2D approach that shows the ability to image a single slice much more quickly than with SEMAC. The use of a spectral localizer scan is a variation of this embodiment that may apply to imaging one or more slices. Obvious distortion and pile-up artifacts in FSE are corrected by the other methods. This embodiment has comparable artifact correction to SEMAC, but lower SNR due to the 2D approach. Using bins above 1% gives about a 60% scan time reduction, and actually reduces noise added from zero-signal bins. The benefit of the localizer would likely be much greater near smaller devices such as surgical clips, dental fillings or titanium screws. Like other MSI methods, residual artifacts from background gradients also exist.

This embodiment demonstrates a "multi-frequency" 2D imaging approach for artifact correction near metallic implants. This is essentially a 2D version of MAVRIC, and similar to a proposed spiral off-resonance correction method. Regions are excited using a well-known gradient reversal between excitation and refocusing, though other excitation options can be used. Current MSI methods use 3D imaging (phase encoding in y and z), which is slow, inflexible, and can induce ringing artifacts with low numbers of phase encodes. Instead, this embodiment directly excites and images frequency bands with phase encoding in a single dimension, offering much faster imaging for limited numbers of slices or limited off-resonance. Further advantages are the lack of need for view-angle-tilting and the ability to acquire selected bins with reduced excite/receive bandwidth, perhaps to improve SNR for the "on-resonance" bin, which typically contains most of the signal. Drawbacks include a lower SNR efficiency with respect to 3D sequences and the need for intelligent interleaving, especially when reduced bin sets are used. Acceleration with parallel imaging, multiband or Hadamard encoding, along with different bin combination methods are all straightforward variations. Overall this embodiment offers a much faster alternative to 3D MSI sequences, with comparable artifact suppression, for many applications of imaging near metal.

This embodiment provides the use of slice-selective and frequency-selective regions, where the former obviates the need for z-axis phase encoding, which is problematic in SEMAC because of the low number of phase encodes, and also inflexible. This embodiment offers the flexibility to image a single slice in far less scan time than MSI methods, since phase encoding is only required in one dimension rather than two. In addition, this embodiment offers a simple, direct way to pre-scan to determine if there is any signal in a slice/frequency bin, so that zero-signal bins could be skipped to save time, whether imaging a few slices or an entire volume. This embodiment provides the ability to essentially use conventional spin echo imaging for the "on-resonance" signal, with low bandwidth if desired, but add extra frequency bands to add artifact correction near the metal.

Other embodiments may trade off between image quality and scan time, and offer utility for different applications. Such embodiments may provide bins that can be overlapped as with other MSI methods, in either slice direction, frequency direction or both. Other embodiments may provide variable bin size that can easily be used, for example to allow a lower readout bandwidth (higher SNR) at certain frequencies. Embodiments may use variable averaging, whereby some bins have different numbers of averages or "NEX". Different forms of a spectrally and spatially selective excitation can be used including varied bandwidths or gradient flips between excitation and refocusing, using a non-spatially-selective pulse for either excitation or refocusing, or using a spectral-spatial excitation or refocusing pulse to limit the bin in two dimensions. Any spin echo or FSE contrast mechanism can be used including T1-weighted, T2-weighted, proton-density-weighted, STIR, FLAIR, fast-recovery, or combinations of the above. Single-shot FSE or HASTE approaches can be used, possibly with variable flip angle approaches. A single-shot technique whereby the scan first images the "on-resonance" bin, then successively adds a broader and broader range of resonances, showing the resulting image, until the user decides it is adequate may simplify user-interface considerations. An embodiment could track when the user stops, and use this information to do a higher-resolution FSE acquisition, interleaving the same acquired bins. Embodiments of the invention may use different interleaving of bins, so that each bin overlaps roughly twice the volume of interest of a multislice scan compared with standard imaging. However, the cross-shaped regions actually allow direct interleaving of all slices at one frequency, for example, with no greater complexity than standard imaging. Embodiments may incorporate view-angle tilting (VAT) to offer some reduction of in-plane artifacts in some cases. Embodiments may use parallel imaging in conjunction with this method, with different approaches to calibrate coil sensitivities. Embodiments may use multiband excitation with Hadamard encoding, which might offer an SNR benefit at the cost of some scan time. Embodiments may use a multi-echo spectral readout, which may offer additional improvement of the pixel-level in-plane distortion that result from a high-bandwidth excitation.

EXAMPLE

Figure 9:
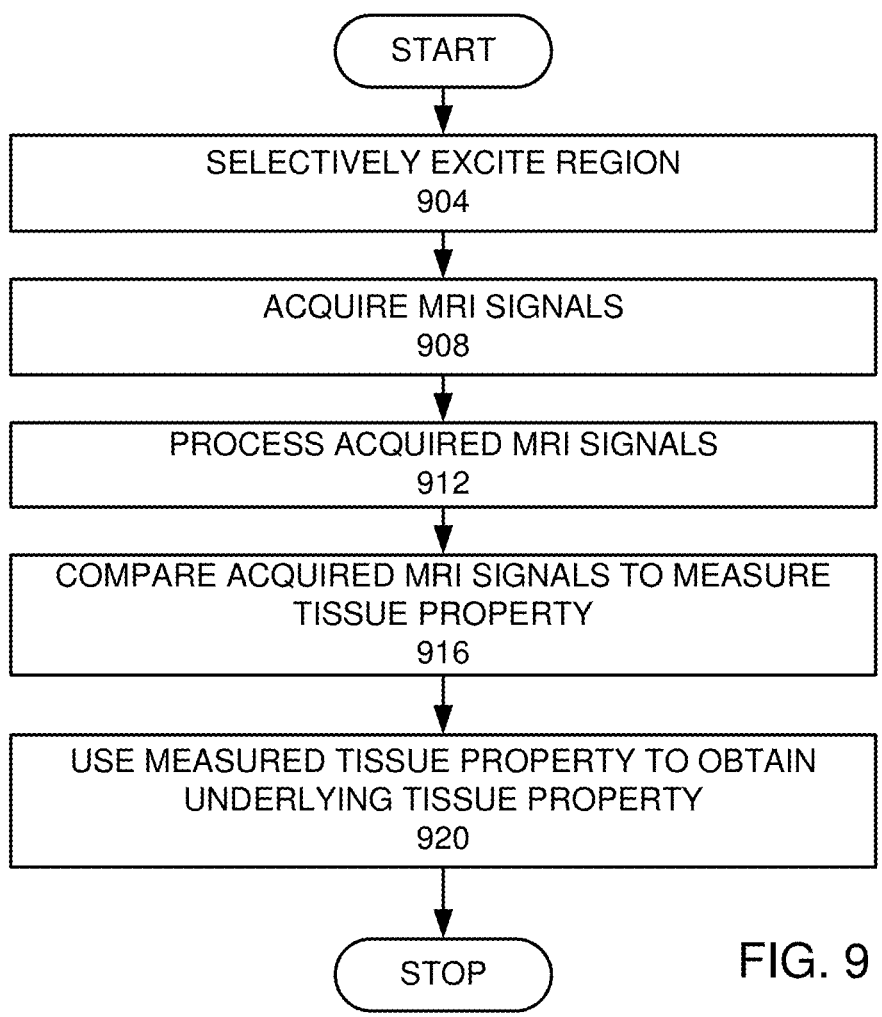
FIG. 9 is a high level flow chart of an embodiment of the invention.

To facilitate understanding, FIG. 9 is a high level flow chart of an embodiment of the invention. A region sufficiently close to a metal object, so that the metal object induces artifacts, is selectively excited using an RF pulse and a selection gradient (step 904). At least one MRI signal is acquired (step 908). The acquired MRI signals are processed to correct for artifacts induced by the metal object (step 912). The acquired MRI signals are compared to measure a tissue property (step 916). The measured tissue property is used to determine an underlying tissue property (step 920). Tissue properties may be T1, proton density, or apparent diffusion coefficient (ADC). A tissue property may also be a combination of multiple tissue properties. Underlying tissue properties are temperature, heat conductivity or magnetic susceptibility, which are derived from the tissue properties. Tissue properties are properties that are measured or derived directly from a MRI process. Underlying tissue properties are properties that are not directly measured or derived from a MRI process, but instead are determined by comparing tissue property values by either comparing different tissue property readings or comparing a tissue property reading to a standard.

Figure 10:
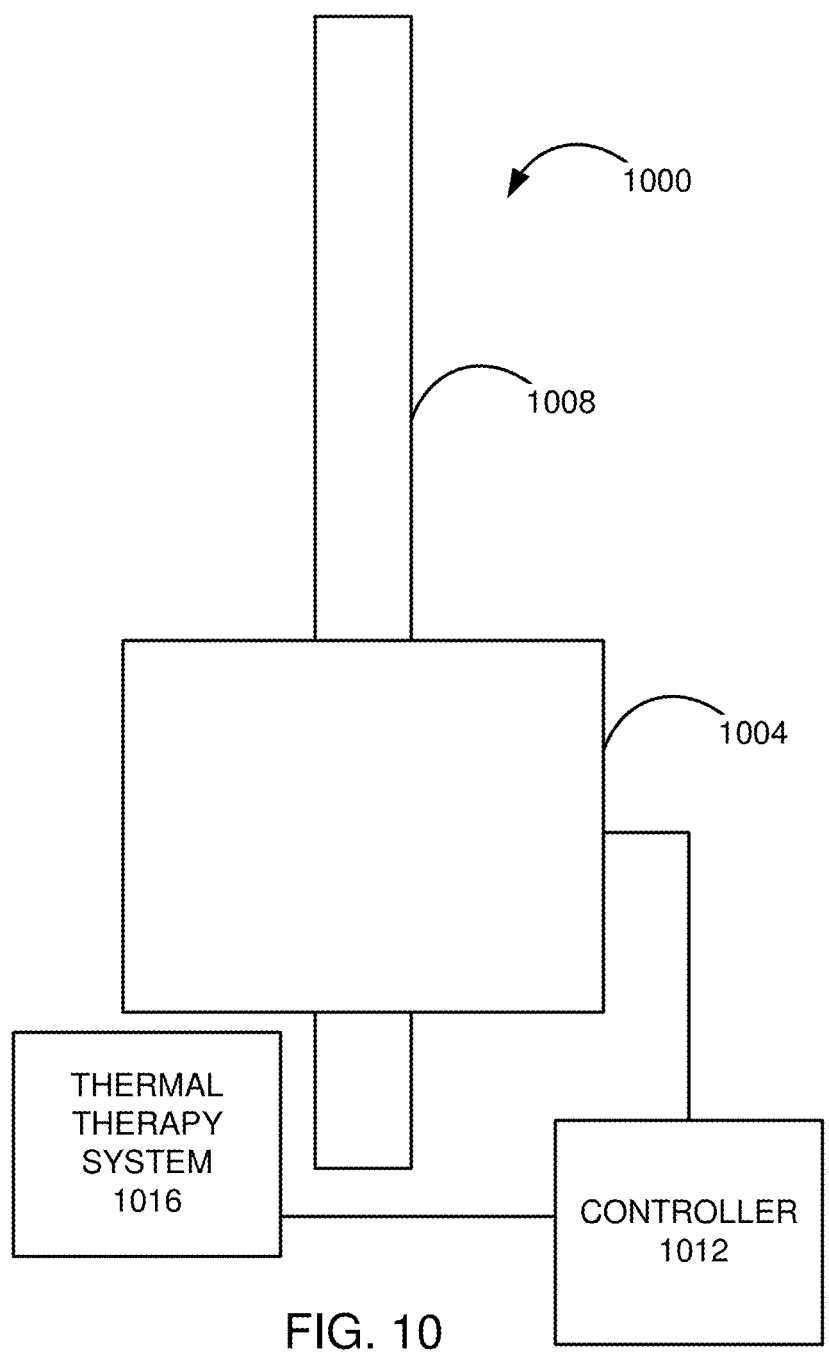
FIG. 10 is a schematic top view of a magnetic resonance imaging (MRI) system that may be used in an embodiment of the invention.

FIG. 10 is a schematic top view of a magnetic resonance imaging (MRI) system 1000 that may be used in an embodiment of the invention. The MRI system 1000 comprises a magnet system 1004, a patient table 1008 connected to the magnet system, and a controller 1012 controllably connected to the magnet system. In one example, a patient would lie on the patient table 1008 with the region to be measured within the magnet system 1004. The controller 1012 would control magnetic fields and radio frequency (RF) signals provided by the magnet system 1004 and would receive signals from detectors in the magnet system 1004. A thermal therapy system 1016 may be placed to provide thermal therapy to the region. The thermal therapy system 1016 may be connected to the controller 1012 to provide information to or receive information from the controller 1012.

Figure 11:
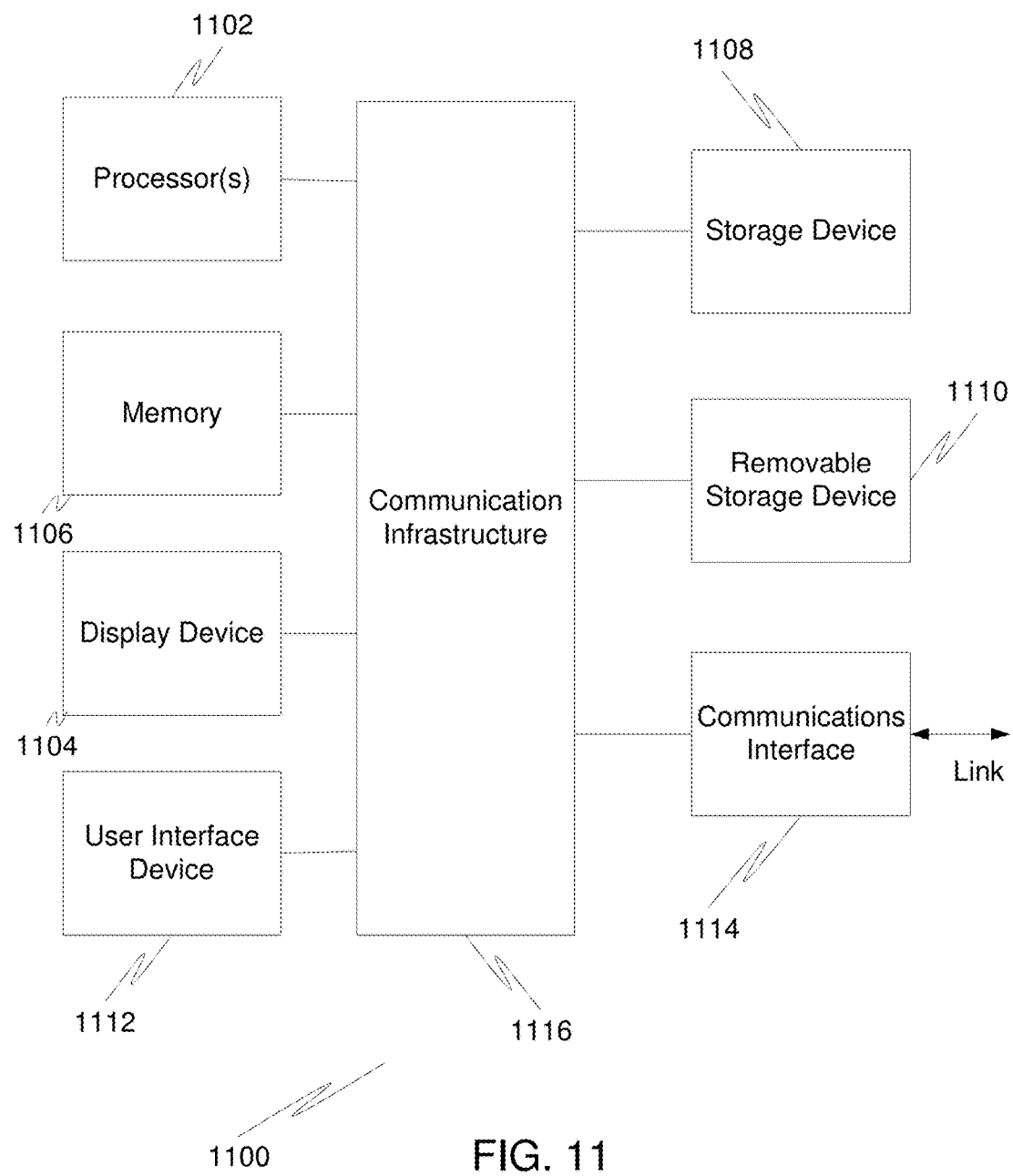
FIG. 11 illustrates a computer system that may be used in an embodiment of the invention.

FIG. 11 is a high level block diagram showing a computer system 1100, which is suitable for implementing the controller 1012 used in embodiments of the present invention. The computer system may have many physical forms ranging from an integrated circuit, a printed circuit board, and a small handheld device up to a super computer. The computer system 1100 includes one or more processors 1102, and further can include an electronic display device 1104 (for displaying graphics, text, and other data), a main memory 1106 (e.g., random access memory (RAM)), storage device 1108 (e.g., hard disk drive), removable storage device 1110 (e.g., optical disk drive), user interface devices 1112 (e.g., keyboards, touch screens, keypads, mice or other pointing devices, etc.), and a communication interface 1114 (e.g., wireless network interface). The communication interface 1114 allows software and data to be transferred between the computer system 1100 and external devices via a link. The system may also include a communications infrastructure 1116 (e.g., a communications bus, cross-over bar, or network) to which the aforementioned devices/modules are connected.

Information transferred via communications interface 1114 may be in the form of signals such as electronic, electromagnetic, optical, or other signals capable of being received by communications interface 1114, via a communication link that carries signals and may be implemented using wire or cable, fiber optics, a phone line, a cellular phone link, a radio frequency link, and/or other communication channels. With such a communications interface, it is contemplated that the one or more processors 1102 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In an embodiment, the measured tissue property is T1 relaxation time and the measured underlying tissue property is temperature. A thermal therapy system 1016 may provide heat to a region near or comprising a metal implant. The thermal system 1016 may use ultrasound or RF to heat the region inside of the body of a patient on the table 1008, such as in MR guided focused ultrasound surgery.

In this embodiment, to measure the temperature of one or more points in the region sufficiently close to a metal implant so that the metal implant induces artifacts, the magnet system 1004 is used to selectively excite at least part of the region (step 904). In this embodiment, excitation and refocusing pulses generated by the magnet system 1004 are used to excite finite spectral and spatial regions. At least one MRI signal is acquired (step 908). In this embodiment, at least one MRI signal is acquired per finite spectral and spatial region. In this example, MRI signals are acquired using a high readout bandwidth for readout of 2D signals, which allows to partially correct for distortions created by the metal implant. The acquired signals are processed to correct for artifacts induced by the metal object (step 912). The processing is able to further remove distortions due to the metal object. The acquired MRI signals are compared to measure at least one tissue property (step 916). In this example, T1 relaxation time is measured. The measured tissue property is used to obtain the underlying tissue property (step 920). In this example, T1 relaxation time sensitivity is used to obtain the underlying tissue property of temperature.

The temperature may be displayed. In this embodiment, the measured temperature is used as a control for the thermal therapy system 1016. For example, if the temperature is too low, then the thermal therapy system 1016 may be adjusted to increase temperature. The temperature may also be used to determine when the thermal therapy is completed. Since the temperature may be determined at different points of the region, the resulting temperature distribution may be used to locate the focal point of ultrasound or RF heating and thus to control where the thermal therapy system is heating. This may be used to selectively increase the temperature at one location, while lowering or maintaining the temperature at another location in the region.

Currently, invasive methods may be used, such as sticking a temperature probe into the region. The number of readings at different location using current methods is limited by the number of temperature probes are placed within a body. This embodiment provides a non-invasive method for measuring the temperature of points in the region.

In certain embodiments, the tissue property is repetitively measured and the underlying tissues property is derived from the change in tissue property. For example, in the above embodiment the tissue property was T1 relaxation time and the underlying tissue property was temperature.

In other embodiments a single measurement of the tissue property may be used to determine the underlying tissue property, without comparing different measurements of the tissue property. The sensitivities may have been previously determined, so that a single measurement of the tissue property may be used to obtain the underlying tissue property. For example, in the above embodiment the tissue property was T1 relaxation time and the underlying tissue property was temperature.

In other embodiments, relative spatial distributions or temporal changes of the underlying tissue property may be directly determined from the at least one acquired MRI signal without explicitly measuring the tissue property. The determined changes of the underlying tissue property may by quantitative or qualitative. In other embodiments, the region contains at least part of a metal object, where the invention is able to measure temperatures in different parts of the region, close to the metal object.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for providing at least one measurement by an MRI system of a tissue property or underlying tissue property in a region sufficiently close to a metal object, so that the metal object induces artifacts, comprising:
   acquiring through the magnetic resonance imaging (MRI) system at least one magnetic resonance imaging signal from the region, wherein the acquiring at least one MRI signal compensates for the artifacts induced by the metal object, wherein the acquiring at least one MRI signal comprises acquiring a plurality of MRI signals from the region, and wherein the acquiring uses a multispectral imaging and wherein the acquiring uses a spatially selective inversion pulse matched to excitation;
   processing the acquired at least one MRI signal to correct for artifacts induced by the metal object;
   extracting at least one tissue property and underlying tissue property measurement by comparing the plurality of MRI signals;

measuring a variation in the at least one tissue property; and using the variation in the at least one tissue property to determine the underlying tissue property measurement, which is temperature.

2. The method, as recited in claim 1, further comprising using the measured tissue property to determine the at least one underlying tissue property.

3. The method, as recited in claim 1, wherein the acquiring of MRI signals is a 2D acquisition.

4. The method, as recited in claim 3, wherein the tissue property is at least one of $T_1$, $T_2$, or proton density.

5. The method, as recited in claim 1, further comprising providing thermal therapy to the region; and using the measured temperature to control the thermal therapy device.

6. The method, as recited in claim 1, wherein the temperature measurement is an absolute temperature measurement.

7. The method, as recited in claim 1, wherein the temperature measurement is a relative temperature measurement.

8. The method, as recited in claim 1, wherein the acquiring at least one MRI signal is used to determine a relative distribution of the underlying tissue property.

9. The method, as recited in claim 1, wherein the acquiring at least one MRI signal comprises acquiring a plurality of MRI signals from the region, and wherein the method further comprises comparing the plurality of MRI signals to measure a relative change of the underlying tissue property.

10. A method for providing a thermal therapy treatment using an MRI system and a thermal therapy device in a region sufficiently close to a metal object, so that the metal object induces artifacts, comprising:

heating the region using the thermal therapy device;

acquiring through the MRI system at least one MRI signal from the region, wherein the acquiring uses a multispectral imaging and wherein the acquiring uses a spatially selective inversion pulse matched to excitation;

processing the acquired at least one MRI signal to correct for artifacts induced by the metal object;

extracting temperature from the processed at least one MRI signal; and changing the heating of the region based on the extracted temperature.

11. A system for providing thermal therapy treatment to a region sufficiently close to a metal object, so that the metal object induces artifacts, comprising:

a thermal therapy device for providing heat to the region;

a MRI system; and a controller comprising:

a central processing unit; and tangible computer readable media, comprising:

computer readable code for heating the region using the thermal therapy device;

computer readable code for acquiring through the MRI system at least one MRI signal from the region, wherein the acquiring uses a multispectral imaging and wherein the acquiring uses a spatially selective inversion pulse matched to excitation;

computer readable code for processing the acquired at least one MRI signal to correct for artifacts induced by the metal object;

computer readable code for extracting temperature from the processed at least one MRI signal; and computer readable code changing the heating of the region based on the extracted temperature.

12. The system, as recited in claim 11, wherein the computer readable code for acquiring through the MRI system at least one MRI signal from the region magnetic resonance imaging system uses a two dimensional multispectral imaging acquisition.

13. The system, as recited in claim 12, wherein the computer readable code for processing at least one MRI signal to correct for artifacts induced by the metal objects corrects for signal loss artifacts and pile-up artifacts induced by the metal objects.

14. The method, as recited in claim 10, wherein the acquiring through the MRI system uses a two dimensional multispectral imaging acquisition.

15. The method, as recited in claim 14, wherein the processing the acquired at least one MRI signal to correct for artifacts induced by the metal objects corrects for signal loss artifacts and pile-up artifacts induced by the metal objects.

16. The method, as recited in claim 1, wherein the acquiring through the magnetic resonance imaging system uses a two dimensional multispectral imaging acquisition.

17. The method, as recited in claim 16, wherein the processing the acquired at least one MRI signal to correct for artifacts induced by the metal objects corrects for signal loss artifacts and pile-up artifacts induced by the metal objects.

18. The method, as recited in claim 16, wherein the two dimensional multispectral imaging acquisition comprises reversing a selection gradient between excitation and refocusing pulses resulting in an excitation of finite spectral and spatial regions to provide reduced distortion near the metal object.

* * * * *

UNITED STATES PATENT AND TRADEMARK OFFICE
CERTIFICATE OF CORRECTION

PATENT NO. : 10,369,385 B2
APPLICATION NO. : 14/686455
DATED : August 6, 2019
INVENTOR(S) : Weber et al.

Page 1 of 1

It is certified that error appears in the above-identified patent and that said Letters Patent is hereby corrected as shown below:

In the Specification

1. Column 1, Line 7, change "contract" to --contracts--.

2. Column 1, Line 7, after "EB017739" and before "awarded" please insert --and EB019723--.

Signed and Sealed this
Twenty-second Day of October, 2019

Andrei Iancu
*Director of the United States Patent and Trademark Office*